United States Patent [19]
Chao et al.

[11] 3,944,584
[45] Mar. 16, 1976

[54] STEROIDAL (16α,17-D)CYCLOHEXENES

[75] Inventors: Sam T. Chao, Cranbury; Christopher M. Cimarusti, Hamilton; Ravi K. Varma, Belle Mead, all of N.J.

[73] Assignee: E. R. Squibb & Sons, Inc., Princeton, N.J.

[22] Filed: Feb. 3, 1975

[21] Appl. No.: 546,647

[52] U.S. Cl. .......... 260/397.3; 260/397.45; 424/243
[51] Int. Cl.² ............................................. C07J 5/00

[58] Field of Search ...... Machine Searched Steroids; 260/397.45, 397.3

*Primary Examiner*—Elbert L. Roberts
*Attorney, Agent, or Firm*—Lawrence S. Levinson; Merle J. Smith; Donald J. Barrack

[57] ABSTRACT

A series of novel steroidal[16α, 17-d]cyclohexenes having a 9-fluoro group is disclosed herein for use as anti-inflammatory agents.

15 Claims, No Drawings

STEROIDAL (16α,17-d) CYCLOHEXENES

SUMMARY OF THE INVENTION

Steroids having the formula

I
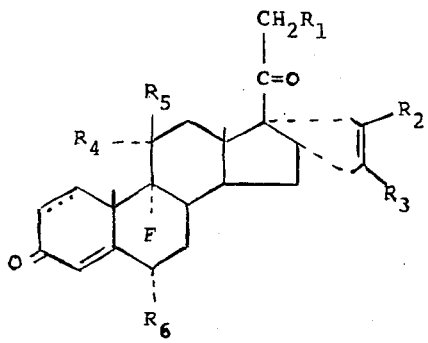

are useful as anti-inflammatory agents. In formula I, and throughout the specification, the symbols are as defined below:

$R_1$ can be hydrogen, hydroxy, halogen or acyloxy;

$R_2$ and $R_3$ can be the same or different and can be hydrogen, alkyl, or aryl;

$R_4$ can be hydrogen and $R_5$ can be hydroxy, or together $R_4$ and $R_5$ can be =O; and $R_6$ can be hydrogen, methyl, or fluorine.

The dotted lines in the 1,2-position of the steroids of this invention represent the optional presence of ethylenic unsaturation.

The term "alkyl", as used throughout the specification, refers to both branched and straight chain alkyl groups having 1 to 8 carbon atoms. Alkyl groups having 1 to 4 carbon atoms are preferred.

The term "aryl", as used throughout the specification, refers to phenyl or phenyl substituted with one or more halogen, alkyl, and alkoxy groups. Phenyl and monosubstituted phenyl are the preferred aryl groups.

The term "acyloxy", as used throughout the specification, refers to groups wherein the acyl portion is a physiologically acceptable acid residue derived from an organic or inorganic acid. Exemplary monocarboxylic acids are those having the formula R-COOH wherein R is alkyl, cycloalkyl, arylalkyl or aryl; e.g., acetic, propionic, valeric, cyclohexanecarboxylic, phenylacetic, benzoic, and toluic acids. Exemplary polycarboxylic acids are malonic, succinic, glutaric, adipic, pimelic, and phthalic acids. Exemplary inorganic acids are sulfuric, nitric, and phosphoric acids. Preferred acyloxy groups are those having the formula alkyl

DETAILED DESCRIPTION OF THE INVENTION

The steroids of formula I are physiologically active substances which possess glucocorticoid and anti-inflammatory activity and hence can be used in lieu of known glucocorticoids in the treatment of rheumatoid arthritis, for which purpose they can be administered in the same manner as hydrocortisone, for example, the dosage being adjusted for the relative potency of the particular steroid. In addition, the steroids of this invention can be used topically in lieu of known glucocorticoids in the treatment of skin conditions such as dermatitis, psoriasis, sunburn, neurodermatitis, eczema, and anogenital pruritus.

When given orally, the compounds of this invention may be used in a daily dosage range of 0.1 to 200 milligrams per 70 kilograms, preferably 0.3 to 100 milligrams per 70 kilograms. If administered topically, the compounds of this invention may be used in the range of 0.01 to 5.0% by weight, preferably 0.05 to 2.0% by weight, in a conventional cream or lotion. The topical mode of administration is preferred.

The steroids of formula I can be prepared using as starting materials steroids having the formula II
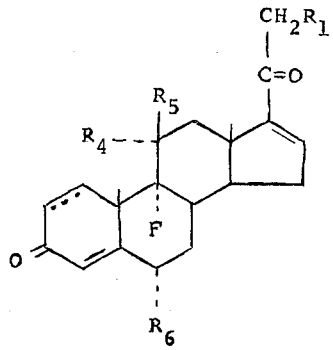

and butadienes having the formula

III 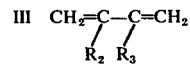

A steroid of formula II and a butadiene of formula III can be reacted to form a steroid of formula I using the DielsAlder reaction. The preferred catalysts for the reaction are anhydrous aluminum chloride and anhydrous aluminum bromide. The reaction can be run in an organic solvent, e.g. a halogenated hydrocarbon such as dichloromethane. The above described Diels-Alder reaction is highly selective and takes place exclusively at the double bond in the 16-position, even in the presence of the $\Delta^{1,4}$-3-keto function. In those instances wherein the butadiene is unstable in the presence of a Lewis acid catalyst, the Diels-Alder reaction is run in the presence of a free radical inhibitor at elevated temperatures.

If the steroid starting material of formula II contains an 11β-hydroxy group, it is desirable to first protect the group before running the Diels-Alder reaction. While many means of protecting the 11-functional group will be apparent to a person skilled in the steroid art, one particularly desirable method is the acylation of the group. The acylation reaction can be run using an acid anhydride, e.g. acetic anhydride in the presence of a Lewis catalyst, e.g. boron trifluoride etherate. After the Diels-Alder reaction has been run, the protective group can be removed using a conventional technique.

Additional methods for the preparation of the compounds of this invention will be readily apparent to a person of ordinary skill in the steroid art. For example, those steroids of this invention having a halogen in the 21-position can be prepared from the corresponding 21-hydroxy steroid by reacting the later with an alkyl or aryl sulfonyl halide (e.g., methanesulfonyl chloride or p-toluenesulfonyl chloride), in the presence of an organic base such as pyridine, to yield a 21-alkyl (or aryl)sulfonyloxy steroid. The 21-alkyl(or aryl)sulfonyloxy steroid intermediate can be reacted with an alkali metal halide (e.g. potassium fluoride, lithium chloride, lithium bromide, sodium iodide, etc.) to yield the corresponding 21-halo steroid.

Using procedures well known to those of ordinary skill in the steroid art it is also possible to prepare a 21-acyloxy steroid of this invention from the corresponding 21-hydroxy steroids. Other variations will be apparent to the practitioner of this invention.

The following examples are specific embodiments of this invention.

EXAMPLE 1

9-Fluoro-11β,21-dihydroxy-1',2'-dimethylpregna-1,4-dieno[16α,17-d]cyclohexene-3,20-dione

A.

11β,21-bis(Acetyloxy)-9-fluoropregna-1,4,16-triene-3,20-dione

A solution of 5 g of 9-fluoro-11β,21-dihydroxypregna-1,4,16-triene-3,20-dione, 21-acetate, 50 ml each of acetic anhydride and dichloromethane and 2.5 ml of boron trifluoride etherate is stirred at room temperature under nitrogen for 2.5 hours. Because the reaction is slow, another 1.5 ml of boron trifluoride etherate is added and the reaction is continued for another 1.5 hours. The resulting solution is diluted with 200 ml of dichloromethane, washed with a saturated sodium bicarbonate solution and water, dried over anhydrous sodium sulfate and evaporated in vacuo to give 5.2 g of a solid. This is chromatographed on a column of 100 g of silica gel. Elution with 1:4 hexane-chloroform gives 4.8 g of material. Crystallization from chloroform-hexane gives 4.2 g of the title compound, melting point 294–296°C.

B.

9-Fluoro-11β,21-dihydroxy-1',2'-dimethylpregna-1,4-dieno[16α,17-d]cyclohexene-3,20-dione A solution of 1.8 g of 11β,21-bis(acetyloxy)-9-fluoropregna-1,4,16-triene-3,20-dione and 600 mg of anhydrous aluminum chloride in 35 ml of dichloromethane is stirred for 1 hour under nitrogen to afford a homogeneous solution. To this is added dropwise a solution of 2,3-dimethyl-1,3-butadiene (3.0 ml) in dry dichloromethane (5.0 ml). After 1 hour the mixture is diluted with dichloromethane (250 ml), washed with a 10% sodium bicarbonate solution and water, dried over anhydrous sodium sulfate, and evaporated in vacuo to give 6.3 g of an oil. This is dissolved in 1:3 hexane-chloroform and chromatographed on a column of silica gel (150 g). Elution with 3:2 hexane-chloroform and 1:1 hexane-chloroform gives 1.8 g of a homogeneous solid. This is dissolved in a mixture of tetrahydrofuran (50 ml) and methanol (40 ml), and a 10% potassium carbonate solution (0.95 ml) is added and stirred under nitrogen at 0°C for 2.0 hours and at room temperature for 4.5 hours. The resulting solution is neutralized with 5% acetic acid. The solvent is then partially removed in vacuo and the slurry is extracted with chloroform. The chloroform solution is washed with water, dried over anhydrous sodium sulfate and evaporated in vacuo to give 1.5 g of a foam. This is dissolved in chloroform and chromatographed on a column of silica gel (60 g). Elution with 1:3 hexane-chloroform and chloroform gives 1.2 g of material. Crystallization from chloroform-hexane gives 760 mg of the title compound, melting point 256°–258°C.

Analysis—Calculated for $C_{27}H_{35}FO_4$: C, 73.27; H, 7.97; F, 4.29. Found: C, 73.08; H, 7.74; F, 4.18.

EXAMPLE 2

21-(Acetyloxy)-9-fluoro-11β-hydroxy-1',2'-dimethylpregna-1,4-dieno[16α,17-d]cyclohexene-3,20-dione A solution of 400 mg of 9-fluoro-11β,21-dihydroxy-1',2'-dimethylpregna-1,4-dieno[16α,17-d]cyclohexene-3,20-dione (prepared as described in Example 1) in 25 ml of pyridine is stirred at room temperature under nitrogen overnight with 0.4 ml of acetic anhydride. The resulting solution is poured into cold 5% hydrochloric acid and extracted with chloroform. The chlorform solution is washed with water, dried over anhydrous sodium sulfate and evaporated in vacuo to give 410 mg of foam. This material is dissolved in 1:4 hexane-chloroform and chromatographed on a 20 g-silica gel column. Elution with 1:3 hexane-chloroform and 1:9 hexane-chloroform followed by crystallization from acetone-hexane gives 320 mg of the title compound, melting point 236°–237°C.

Analysis—Calculated for $C_{29}H_{37}FO_5$: C, 71.87; H, 7.70; F, 3.92. Found: C, 72.17; H, 7.66; F, 3.75.

EXAMPLE 3

21-Chloro-9-fluoro-11β-hydroxy-1',2'-dimethylpregna-1,4-dieno[16α,17-d]cyclohexene-3,20-dione

A.

9-Fluoro-11β-hydroxy-21-mesyloxy-1',2'-dimethylpregna-1,4-dieno[16α,17-d]cyclohexene-3,20-dione A solution of 400 mg of 9-fluoro-11β,21-dihydroxy-1',2'-dimethylpregna-1,4-dieno[16α,17-d]cyclohexene-3,20-dione (prepared as described in example 1) in 20 ml of pyridine is stirred at 0°C under nitrogen for 6 hours with 0.4 ml of methanesulfonyl chloride. The resulting solution is poured into cold 5% hydrochloric acid and extracted with chloroform. The chloroform solution is washed with water, dried over anhydrous sodium sulfate and evaporated in vacuo to give 490 mg of the title compound.

B.

21-Chloro-9-fluoro-11β-hydroxy-1',2'-dimethylpregna-1,4-dieno[16α,17-d]cyclohexene-3,20-dione A solution of 490 mg of 9-fluoro-11β-hydroxy-21-(mesyloxy)-1',2'-dimethylpregna-1,4-dieno[16α,17-d]cyclohexene-3,20-dione and 500 mg of lithium chloride in 35 ml of dimethylformamide is refluxed for 2 hours under nitrogen. The resulting solution is cooled, poured into ice-water and stirred for 30 minutes. The solid is filtered and dissolved in chloroform. The chloroform solution is washed with 5% hydrochloric acid, water, dried over anhydrous sodium sulfate and evaporated in vacuo to give 290 mg of residue. This is dissolved in 1:3 hexane-chloroform and chromatographed on a 20 g-silica gel column. Elution with 2:3 hexane-chloroform and 1:4 hexane-chloroform gives 280 mg of material. Crystallization from acetone-hexane gives 250 mg of the title compound, melting point 236–237°C.

Analysis—Calculated for $C_{27}H_{34}ClFO_3$: C, 70.34; H, 7.43; Cl, 7.69; F, 4.12.

Found: C, 70.28; H, 7.28; Cl, 7.55; F, 3.97.

EXAMPLE 4

9-Fluoro-11β,21-dihydroxypregna-1,4-dieno-[16α,17-d]cyclohexene-3,20-dione

A solution of 1.4 g of 11β,21-bis(acetyloxy)-9-fluoropregna-1,4,16-triene-3,20-dione (prepared as described in example 1A) and 550 mg of anhydrous alumium chloride in 30 ml of dichloromethane is stirred under a condensor (cooled with ice-acetone) for 1 hour at room temperature under nitrogen to afford a homogeneous solution. 1,3-Butadiene (4–5 ml) is condensed by the ice-acetone condensor and is added dropwise to the above homogeneous solution and stirred for 25 minutes. After the addition of 1,3-butadiene in the same manner three more times, the solution is stirred overnight at room temperature under nitrogen. The resulting mixture is diluted with 200 ml of chloroform, washed with a saturated sodium bicarbonate solution and water, dried over anhydrous sodium sulfate and evaporated in vacuo to give 1.8 g of a foam. This is dissolved in 2:3 hexane-chloroform and is chromatographed on a column of silica gel (50 g). Elution with 2:3 hexane-chloroform gives 1.5 g of material. This is dissolved in a mixture of tetrahydrofuran (50 ml) and methanol (30 ml) and a 10% potassium carbonate solution (1.0 ml) is added and stirred under nitrogen at room temperature overnight. The resulting solution is neutralized with 5% acetic acid and evaporated in vacuo. The slurry is diluted with water and extracted with chloroform. The chloroform solution is washed with water, dried over anhydrous sodium sulfate and evaporated in vacuo to give 1.6 g of a foam. This is dissolved in 1:4 hexane-chloroform and chromatographed on a 30 g-silica gel column. Elution with 1:4 hexane-chloroform and chloroform gives 910 mg of material. Crystallization from chloroform-hexane gives 630 mg of the title compound, melting point 244–245°C.

Analysis—Calculated $C_{25}H_{31}FO_4$: C, 72.44; H, 7.54; F, 4.58.

Found: C, 72.33; H, 7.37; F, 4.49.

EXAMPLE 5

21-(Acetyloxy)-9-fluoro-11β-hydroxypregna-1,4-dieno[16α,17-d]cyclohexene-3,20-dione A solution of 300 mg of 9-fluoro-11β,21-dihydroxypregna-1,4-dieno[16α,17-d]cyclohexene-3,20-dione (prepared as described in example 4) in 10 ml of pyridine and 0.2 ml of acetic anhydride is stirred at room temperature under nitrogen overnight. The resulting solution is poured into cold 5% hydrochloric acid and extracted with chloroform. The chloroform solution is washed with water, dried over anhydrous sodium sulfate and evaporated in vacuo to give 350 mg of a foam. This is dissolved in 1:3 hexane-chloroform and chromatographed on a column of silica gel (20 g). Elution with 1:3 hexane-chloroform and crystallization from acetone-hexane gives 230 mg of the title compound, melting point 187–188°C.

Analysis—Calculated for $C_{27}H_{33}FO_5$: C, 71.02; H, 7.29; F, 4.12.

Found: C, 71.01; H, 7.14; F, 3.95.

EXAMPLE 6

21-Chloro-9-fluoro-11β-hydroxypregna-1,4-dieno[16α,17-d]cyclohexene-3,20-dione

A.

9-Fluoro-11β-hydroxy-21-(mesyloxy)-pregna-1,4-dieno[16α,17-d]cyclohexene-3,20-dione A solution of 450 mg of 9-fluoro-11β,21-dihydroxypregna-1,4-dieno[16α,17-d]cyclohexene-3,20-dione (prepared as described in example 4) in 10 ml of pyridine is stirred at 0°C under nitrogen for 4 hours with 0.4 ml of methanesulfonyl chloride. The resulting solution is poured into cold 5% hydrochloric acid and extracted with chloroform. The chloroform solution is washed with water, dried over anhydrous sodium sulfate and evaporated in vacuo to give 550 mg of the title compound.

B.

21-Chloro-9-fluoro-11β-hydroxypregna-1,4-dieno[16α,17-d]cyclohexene-3,20-dione

A solution of 550 mg of 9-fluoro-11β-hydroxy-21-(mesyloxy)-pregna-1,4-dieno[16α,17-d]cyclohexene-3,20-dione and 600 mg of lithium chloride in 30 ml of dimethylformamide is refluxed for 2 hours under nitrogen. The resulting solution is cooled, poured into ice-water, and stirred for 30 minutes. The solid is filtered and dissolved in chloroform. The chloroform solution is washed with 5% hydrochloric acid and water, dried over anhydrous sodium sulfate and evaporated in vacuo to give 0.6 g of a residue. This is dissolved in 2:3 hexane-chloroform and chromatographed on a silica gel column (20 g). Elution with 3:2 chloroform-hexane and 4:1 chloroform-hexane gives 360 mg of material. Crystallization from acetone-hexane gives 270 mg of the title compound, melting point 256°–257°C.

Analysis—Calculated for $C_{25}H_{30}ClFO_3$: C, 69.35; H, 6.98; Cl, 8.19; F, 4.39.

Found: C, 69.07; H, 6.77; Cl, 8.09; F, 4.19.

EXAMPLE 7

9-Fluoro-1',2'-dimethylpregn-4-eno-[16α,17-d]cyclohexene-3,11,20-trione

A. 9-Fluoropregna-4,16-diene-3,11,20-trione

To a solution of 8.5 ml of dry pyridine in 220 ml of dry dichloromethane is added 5.1 g of chromium trioxide in small portions. When all the solid has dissolved, 25 g of dry Celite is added followed (with stirring) by a solution of 3.0 g of 9-fluoro-11β-hydroxypregna-4,16-diene-3,20-dione. The mixture is then stirred at room temperature for 30 minutes, filtered and the solids are washed with a small amount of dichloromethane. The filtrate and the washings are combined, washed with 5% hydrochloric acid, a dilute sodium bicarbonate solution and water, dried and evaporated to afford the product as a solid. One crystallization from acetone-hexane gives 2.65 g of the title compound, melting point 208°–211°C.

B.

9-Fluoro-1',2'-dimethylpregn-4-eno-[16α,17-d]cyclohexene-3,11,20-trione

To a suspension of 15 mg of anhydrous aluminum chloride in 4.0 ml of dry dichloromethane is added a solution of 200 mg of 9-fluoropregna-4,16-diene-3,11,20-trione and 0.4 ml of 2,3-dimethyl-1,3-butadiene. The solution is then stirred at room temperature for 68 hours. The reaction is continued for an additional 24 hours after the addition of 5.0 ml of dichloromethane, 55 mg of anhydrous aluminum chloride and 0.4 ml of 2,3-dimethylbutadiene. The mixture is then poured into water and extracted with chloroform. The chloroform extract is washed with a 10% sodium carbonate solution and water, dried and evaporated to afford a mixture of the starting material and the product. Isolation of the product and crystallization from acetone-hexane gives the title compound, melting point 202°–203°C.

EXAMPLE 8

9-Fluoro-11β,21-dihydroxy-2'-phenylpregna-1,4-dieno[16α,17-d]cyclohexene-3,20-dione A solution of 1.0 g of 11β,21-bis(acetyloxy)-9-fluoropregna-1,4,16-triene-3,20-dione (prepared as described in example 1A), 1.5 g of 2-phenyl-1,3-butadiene and 220 mg of 4,4)-thiobis-6-tert-butyl-m-cresol in 25 ml of diethylbenzene is stirred at 195°C under nitrogen for 20 hours. To this is added 0.2 ml of 2-phenyl-1,3-butadiene every 3 hours until 2.8 ml has been added. The diethylbenzene is then distilled off in vacuo to leave an oil. This is dissolved in 3:2 chloroform-hexane and passed through a 30 g-silica gel column. Elution with 3:2 chloroform-hexane gives 1.15 g of material. This is again dissolved in 3:2 chloroform-hexane and chromatographed on a 45 g-silica gel column. Elution with 1:1 chloroform-hexane gives 960 mg of material. This is dissolved in 1:1 tetrahydrofuran-methanol and a 10% potassium carbonate solution (1.0 ml) is added and stirred under nitrogen at room temperature overnight. The resulting solution is neutralized with 5% acetic acid. The solvent is partially removed in vacuo and the slurry is diluted with water and extracted with chloroform. The chloroform solution is washed with water, dried over anhydrous sodium sulfate and evaporated in vacuo to give 710 mg of foam. This is dissolved in 1:3 hexane-chloroform and chromatographed on a 50 g-silica gel column. Elution with 1:3 hexane-chloroform and 1:9 hexane-chloroform gives 494 mg of material. Crystallization from ethyl acetate-hexane gives 305 mg of the title compound, melting point 255°–256° C.

Analysis—Calculated for $C_{31}H_{35}FO_4$: C, 75.89; H, 7.19; F, 3.87.

Found: C, 75.83; H, 7.03; F, 4.17.

EXAMPLE 9

21-(Acetyloxy)-9-fluoro-11β-hydroxy-2'-phenylpregna-1,4-dieno[16α,17-d]cyclohexene-3,20-dione A solution of 286 mg of 9-fluoro-11β,21-dihydroxy-2'-phenylpregna-1,4-dieno[16α,17-d]cyclohexene-3,20-dione (prepared as described in example 8) and 0.25 ml of acetic anhydride in 20 ml of pyridine is stirred at room temperature under nitrogen for 2.5 hours. The resulting solution is poured into cold 5% hydrochloric acid and extracted with chloroform. The chloroform solution is washed with water, dried over anhydrous sodium sulfate and evaporated in vacuo to give a foam. This is dissolved in 1:9 hexane-chloroform and chromatographed on a 40 g-silica gel column. Elution with chloroform-hexane (4:1, 3:1, and 9:1) gives 226 mg of material. Crystallization from ethyl acetate-hexane gives 194 mg of the title compound, melting point 145°–146°C.

Analysis—Calculated for $C_{33}H_{37}FO_5$: C, 74.41; H, 7.00; F, 3.57.

Found: C, 74.26; H, 6.88; F, 3.60.

EXAMPLES 10–13

Following the procedure of example 1, but substituting the steroid listed in column I for 9-fluoro-11β,21-dihydroxypregna-1,4,16-triene, 21-acetate and the butadiene listed in column II for 2,3-dimethyl-1,3-butadiene, the steroid listed in column III is obtained.

| Example | Column I | Column II | Column III |
|---|---|---|---|
| 10 | 6α,9-difluoro-11β,21-dihydroxypregna-1,4,16-triene-3,20-dione, 21-acetate | 2,3-diphenyl-1,3-butadiene | 6α,9-difluoro-11β,21-dihydroxy-1',2'-diphenylpregna-1,4-dieno[16α,17-d]cyclohexene-3,20-dione |
| 11 | 9-fluoro-11β,21-dihydroxy-6α-methylpregna-4,16-diene-3,20-dione, 21-acetate | 2,3-di-(p-chlorophenyl)-1,3-butadiene | 1',2'-di-(p-chlorophenyl)-9-fluoro-11β,21-dihydroxy-6α-methylpregn-4-eno[16α,17-d]-cyclohexene-3,20-dione |

What is claimed is:

1. A steroid having the formula

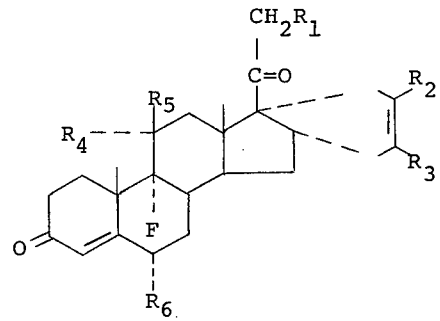

or the 1,2-dehydro derivative thereof, wherein $R_1$ is hydrogen, hydroxy, halogen, or acyloxy; $R_2$ and $R_3$ are the same or different and are hydrogen, alkyl, or aryl; $R_4$ is hydrogen and $R_5$ is hydroxy, or together $R_4$ and $R_5$ are =O; and $R_6$ is hydrogen, methyl, or fluorine.

2. A steroid in accordance with claim 1 wherein $R_2$ and $R_3$ are both hydrogen.

3. A steroid in accordance with claim 1 wherein $R_2$ and $R_3$ are both alkyl.

4. A steroid in accordance with claim 1 wherein $R_4$ is hydrogen and $R_5$ is hydroxy.

5. A steroid in accordance with claim 1 wherein together $R_4$ and $R_5$ are =O.

6. A steroid in accordance with claim 1 wherein $R_6$ is hydrogen.

7. The steroid in accordance with claim 1 having the name 9-fluoro-11β,21-dihydroxy-1',2'dimethylpregna-1,4-dieno[16α,17-d]cyclohexene-3,20-dione.

8. The steroid in accordance with claim 1 having the name 21-(acetyloxy)-9-fluoro-11β-hydroxy-1′,2′-dimethylpregna-1,4-dieno[16α,17-d]cyclohexene-3,20-dione.

9. The steroid in accordance with claim 1 having the name 21-chloro-9-fluoro-11β-hydroxy-1′,2′-dimethylpregna-1,4-dieno[16α,17-d]cyclohexene-3,20-dione.

10. The steroid in accordance with claim 1 having the name 9-fluoro-11β,21-dihydroxypregna-1,4-dieno[16α,17-d]-cyclohexene-3,20-dione.

11. The steroid in accordance with claim 1 having the name 21-(acetyloxy)-9-fluoro-11β-hydroxypregna-1,4-dieno[16α,17-d]cyclohexene-3,20-dione.

12. The steroid in accordance with claim 1 having the name 21-chloro-9-fluoro-11β-hydroxypregna-1,4-dieno[16α,17-d]cyclohexene-3,20-dione.

13. The steroid in accordance with claim 1 having the name 9-fluoro-1′,2′-dimethylpregn-4-eno[16α,17-d]cyclohexene-3,11,20-trione.

14. The steroid in accordance with claim 1 having the name 9-fluoro-11β,21-dihydroxy-2′-phenylpregna-1,4-dieno[16α,17-d]cyclohexene-3,20-dione.

15. The steroid in accordance with claim 1 having the name 21-(acetyloxy)-9-fluoro-11β-hydroxy-2′-phenylpregna-1,4-dieno[16α,17-d]cyclohexene-3,20-dione.

\* \* \* \* \*